United States Patent [19]

Fosslien

[11] Patent Number: 4,691,580
[45] Date of Patent: Sep. 8, 1987

[54] FLUID SAMPLING APPARATUS

[75] Inventor: Egil Fosslien, 1499 Shermer Rd., Northbrook, Ill. 60062

[73] Assignee: Egil Fosslien, Northbrook, Ill.

[21] Appl. No.: 817,077

[22] Filed: Jan. 8, 1986

[51] Int. Cl.[4] .................. G01N 1/14; G01N 35/08
[52] U.S. Cl. ................... 73/864.84; 422/103; 251/7; 137/625.48; 137/625.4
[58] Field of Search ............ 73/864.83, 864.84; 422/103; 251/7, 4; 137/625.48, 625.4, 613

[56] References Cited

U.S. PATENT DOCUMENTS

| 2,069,261 | 2/1937 | Monnet . | |
|---|---|---|---|
| 2,146,917 | 2/1939 | Rosenberger . | |
| 2,182,724 | 12/1939 | Hennessy | 137/613 X |
| 2,349,403 | 5/1944 | Bertetti . | |
| 2,645,245 | 7/1953 | Maisch . | |
| 3,395,838 | 8/1968 | Beres et al. . | |
| 3,543,791 | 12/1970 | Fox et al. | 251/7 X |
| 3,607,082 | 9/1971 | Thiers | 251/7 X |
| 3,643,511 | 2/1972 | Warncke et al. | 73/864.83 X |
| 3,933,165 | 1/1976 | Budzak et al. | 137/625.48 |
| 3,974,858 | 8/1976 | Nielsen | 251/7 X |
| 3,976,277 | 8/1976 | Basel et al. | 251/7 |
| 4,120,662 | 10/1978 | Fosslien | 422/63 X |
| 4,128,008 | 12/1978 | Linenberg | 73/864.83 X |
| 4,138,089 | 2/1979 | McCarthy | 137/625.48 X |
| 4,259,985 | 4/1981 | Bergmann | 251/7 X |
| 4,284,103 | 8/1981 | Pemberton | 137/625.4 X |
| 4,311,484 | 1/1982 | Fosslien | 73/864.21 |
| 4,458,541 | 7/1984 | Deming et al. | 73/864.83 |
| 4,493,476 | 1/1985 | Strickland et al. | 137/625.48 X |

FOREIGN PATENT DOCUMENTS

4324 10/1979 European Pat. Off. ............. 251/4

Primary Examiner—Tom Noland

[57] ABSTRACT

A T-valve and a reciprocating sliding valve are utilized in lines running from an automated sampler apparatus to an analyzer apparatus. The T-valve, the sampler, the analyzer and sliding valve maintain an air bubble in the lines to assure separation between successive liquid samples running between the sampler to the analyzer or an individual sample container and the analyzer in a manual mode, the T-valve and reciprocating sliding valve permitting alternative withdrawal of samples from the automated sampler or the container in manual mode.

20 Claims, 19 Drawing Figures

FLUID SAMPLING APPARATUS

BACKGROUND OF THE INVENTION

1. Field of the Invention

This invention relates to a fluid sampling apparatus, and more particularly, to an apparatus for obtaining a liquid sample such as a specimen of blood or the like and for delivering the sample to means for analyzing it.

2. Description of Related Art

Preparatory to analysis, a sample of whole blood is drawn from a patient and typically stored under negative pressure (i.e., a pressure less than atmospheric) in a glass tube with a rubber stopper, such as the type sold under the trade designation 'Vacutainer' by Becton-Dickenson and Company of East Rutherford, N.J. The blood in this tube is gently and carefully mixed to obtain an even distribution of blood cells either by use of a separate mixing device followed by removal of the rubber stopper and aspiration of an aliquot of blood into a blood analyzer, or by automated mixing and subsequent sampling from a closed container using devices such as described in my U.S. Pat. No. 4,120,662 and my U.S. Pat. No. 4,311,484 (the '484 patent).

The specimen sampling apparatus described in the '484 patent mixes the contents of a series of specimen tubes and delivers them sequentially to a sampling station where a needle, which is connected via a conduit to the intake of a suitable analyzer such as a "Coulter Counter" Model S By Coulter Electronics, Inc. of Hialeah, Fla., penetrates the rubber stopper for aspiration of a specimen sample from the tube into the needle and thence through a conduit with subsequent delivery of blood to the analyzer blood metering system.

Typically, in using the Coulter Counter Model S, 1 ml of blood would be drawn from the storage tube and transported through the lines of the apparatus with about 0.044 ml of blood actually being subjected to dilution for analysis. In many of these apparatuses, various blood samples could and did abut one another in the lines or conduits of the sample probe and blood metering valve of the apparatus while the blood was being transported from the sample container to the portion of the apparatus which metered the blood for subsequent dilution and analysis. With relatively larger amounts of blood flowing through the blood analyzer sample metering system, various blood samples could without harm abut at certain points in the blood lines or conduits of the blood analyzer. This abutment of samples resulted in a certain tolerable amount of longitudinal mixing between samples. Because larger amounts of each blood sample flowed through the lines of the blood analyzer metering system, the blood subjected to longitudinal mixing was practically not subjected to analysis by the analyzer in the pragmatic sense when blood was presented to the blood analyzer manually or by the automatic sampling apparatus. Rather, blood subject to such mixing at blood sample interfaces was simply "swept" through the blood analyzer aspiration lines and blood metering valve until nearly unmixed blood reached the latter valve for dilution of the blood and subsequent analysis of blood parameters.

Blood analyzers now have been developed which require very little blood for analysis. However, with smaller sample volumes drawn, cross contamination from one sample to the subsequent sample through longitudinal mixing of the samples in the lines of the blood analyzer sample aspiration probe and blood metering valve becomes a concern, and these newer analyzers therefore use a saline rinse of the aspiration probe and the metering valve and tubing between blood samples. When blood is aspirated through the blood analyzer sampling probe following the saline rinse, there is some longitudinal mixing of saline and the aspirated blood unless means for separation of the saline and blood are employed. To reduce this saline-to-blood-sample carry-over some devices introduce a small segment of air or other gas between the saline and the blood. Heretofore, however, segments of air or other gas have not been used to separate samples in apparatuses which have both an automated and manual aspiration mode. As will be discussed infra, a compatability problem for consistent results between such two modes has existed when gas separation of samples has been attempted in apparatuses which sample both manually and automatically.

Analyzers which use very small amounts of blood (100 microliters) are, for instance, the ELT-800 or ELT-1500 manufactured by Ortho Diagnostic Systems of Westwood, Mass. These analyzers aspirate a small amount of air between the saline rinse liquid and the blood samples to reduce the carry-over from blood to saline during the saline intersample rinse and from saline to blood aspirated into the blood metering valve. The air bubble separates the saline and blood and practically eliminates cross contamination of samples through longitudinal mixing. The air bubble separation is needed simply because larger sample volumes are not available to be "swept" through the lines of the blood metering valve of the blood analyzer to present uncontaminated blood for metering by the analyzer metering valve, for subsequent dilution and analysis.

Analyzers such as the ELT-1500 only permit manual aspiration of blood without automated sampling from closed containers. Automated sampling from closed containers is of importance to reduce the health risk caused by aerosol formation from work with open blood containers as well as a means of cost reduction through automating the process of blood mixing and introduction of aliquots of blood into the blood analyzer. To understand the design requirements for a system for automatic sample introduction from a sampling system such as that described in my '484 patent and into a blood analyzer such as the ELT-1500, it is necessary to understand how blood is manually aspirated and metered in the ELT. An aliquot of sample is aspirated through a sip tube immersed in mixed whole blood contained in an open tube, and the aspirated blood is split into approximately equal portions each of which is drawn through a whole-blood metering tubing having a predetermined length. The blood in each loop is diluted separately. Blood from one loop is diluted and used for white cell enumeration. Blood from the other loop is diluted and used for hemoglobin determination, and after further dilution, for enumeration of red blood cells as well of blood platelets. During manual aspiration of whole-blood into the metering valve, blood is drawn a predetermined length past the metering loops (post-loop distance, PLD). It is critical for accuracy and precision of analytical results that the PLD is consistent for all samples. The PLD depends upon the relationship of the volume of whole-blood aspirated by the analyzer sample aspiration pumps as well as the inside diameter and the length of the sip tube. The critical nature of the post-loop distance is probably due to minute saline-toblood carry-over as well as a longitudinal concentration gradient of blood components within the whole-blood aspiration tubing near the leading edge end of the blood in said tubing.

To fulfil the above criteria for analytical precision and accuracy, a system for aspiration of whole-blood using an automated mixing and sampling device must therefore expose the automatically introduced blood to conditions practically identical to those occurring when using the manual-sip tube. The tubing used for automated introduction of whole-blood samples (auto-sip tube) must therefore have practically the same diameter and length as the manual-sip tube. To switch from manual to automated whole-blood aspiration into the whole-blood metering valve in the analyzer, a valve must be installed which either connects the manual-sip tube or the auto-sip tube to the metering valve.

To achieve sampling conditions which are consistent between automated and manual modes for consistent analysis, a valving system is needed to isolate the vacuum used for drawing an aliquot of blood from the closed container and for allowing aspiration of part of this sample into the blood analyzer blood metering system under conditions permitting an intact air bubble between saline and samples.

Since blood is drawn from the vacutainer under negative pressure and this negative pressure would disrupt the small air bubble used for carry-over reduction in the auto-sip tube as well as the anaylzer metering valve, means are needed to isolate the vacuum from the analyzer sip tube tip during vacuum assisted aspiration of whole blood from the vacutainer in an automated blood mixing and sampling device such as described in my '484 patent.

To achieve the sample separation for analyzers using small amounts of blood the use of relatively large and/or complicated valves has been attempted. These valves have been disadvantageous because as relatively big valves, more dead volume exists within them which consumes much of an already small sample for operation; as relatively big valves, the more force they consume to open and close; and because they are complicated, they generally are more costly.

It is an object of the present invention to provide a sampling device for fluid materials which will permit the sampling of materials without the longitudinal mixing thereof.

It is another object of the invention to provide valves in a fluid handling and metering system which are easily cleaned, have very small or zero dead volumes, are easily manufactured and require only small forces to open and close.

It is another object of this invention to provide a fluid sampling system which permits automated and manual sample introduction into an analyzer under similar conditions for minimal differences in analytical results generated by the analysis of the samples regardless of whether the sample is introduced manually or automatically.

It is another object of this invention to provide a T-valve for the valving of a fluid flow which is self cleaning, has a very small or zero dead volume, is easily manufactured and requires only a small force to open and close.

It is still another object of this invention to provide a reciprocating, sliding valve for the valving of fluid flow which has a small sliding surface, is self-aligning with a valve seat member, has a straight flow path and is resistant to sticking.

BRIEF DESCRIPTION OF THE DRAWINGS

These and other objects and features of the invention will be apparent from the following description and drawings in which:

FIGS. 8 through 12 are diagrammatic views illustrating the sequence of steps involved in obtaining a sample of blood or the like from a container and delivering it to the analyzer, the specimen sample being shown in solid lines and cleaning solution being shown in broken lines; and FIGS. 8A through 12A are diagrammatic views of a portion of a cross section of the T-valve of the invention showing whether the T-valve is open or closed and the air bubble therein.

SUMMARY OF THE INVENTION

According to the invention, an air bubble is used to reduce cross mixing of saline wash with blood samples and separate blood samples; assist in equalizing the amounts of blood drawn into metering loops and helps maintain identical flow characteristics of the blood into the analyzer in both an automated aspiration mode and manual aspiration mode.

In accordance with the present invention, a T-valve and a reciprocating sliding aspiration mode valve are utilized in lines running from a sampler apparatus to an analyzer apparatus, the aspiration mode valve permitting sampling of fluid from an automatic sampler sequentially feeding a plurality of containers to a sampling station for the withdrawal of liquid therefrom, alternatively the aspiration mode valve permitting sampling of fluid from a container in a manual mode. The T-valve has a particular construction and characteristics which provide a valve with little or no dead volume, is easily cleaned, is simple and easily constructed, requires only a small force to open and close and creates in the cycle of the sampler with the analyzer an air bubble in the lines between the sampler and analyzer such that small liquid samples may be separately transported in lines running from the sampler to the analyzer without longitudinal mixing. The T-valve comprises a first resilient tube defining an interior passage; a second tube, which is preferably rigid and transverse to the longitudinal axis of the first resilient tube, has an orifice at each end and extends through the wall of the resilient tube so that one orifice of the second tube lies about half way through the interior passage of the resilient tube; and means for deforming the interior wall of the resilient tube to sealingly engage the orifice of the second tube extending through the wall of the resilient tube leaving at least one reduced interior passage in the resilient tube, the deformation means comprising a pinch member exterior to the resilient tube and operably connected to means for actuating the pinch member opposite the orifice of the second tube. Preferably the pinch member is transverse to the longitudinal axis of the resilient tube and is adapted to abut the outer wall of the resilient tube to sealingly engage the interior wall of the resilient tube with the orifice of the second tube upon actuation of the pinch member to resiliently deform the interior wall of the resilient tube into abutting engagement with the orifice in the interior passage of the resilient tube. More particularly and preferably, the pinch member is a plunger on a reciprocating member such as an air cylinder. As will be more fully herein described, the aforedescribed T-valve, the sampler, and sliding aspiration mode valve described herein, will maintain an air bubble in such lines to assure separation between successive liquid samples and reduce cross mixing of saline and blood running between the samples to the analyzer.

The aspiration mode valve is a reciprocating sliding valve which includes a housing, a longitudinal channel through the housing, a sliding member extending through the channel in the housing for receiprocating movement therein, the sliding member having at least two channels which are generally normal to the longitudinal channel and which extend through the sliding member, a valve seat which abuttingly engages the sliding member generally normal to the sliding member, the seat including at least one longitudinal channel which provides a generally straight fluid flow through the sliding valve when it is aligned with each one of the channels in the sliding member upon reciprocating movement of the sliding member. The sliding aspiration mode valve also includes means for actuating the sliding member for reciprocating movement, such as a pneumatic or hydraulic piston and cylinder at each end of the sliding member, for reciprocation of the sliding member for fluid communication between the analyzer apparatus and automated sampler or an individual sample container in a manual mode of a sampling-analysis apparatus. The sliding aspiration mode valve of the invention provides a valve which has very little dead volume, a straight fluid path, and is resistant to sticking, self-aligning and has a small sliding surface. Moreover, the T-valve and sliding valve in combination provide a sampling-analysis apparatus which uses an air pocket or bubble to separate samples for analysis. As a result of such separation and valve combination, the sampling-analysis apparatus can sample and analyze small samples compatibly providing consistent results in an automated mode which sequentially feeds a plurality of sample containers to a feeding station for the withdrawal of liquid therefrom, or alternatively, in a manual mode with the withdrawal of liquid from an individual container for analysis. In each case the air bubble proceeds and separates the samples for analysis.

DESCRIPTION OF THE PREFERRED EMBODIMENTS

Figures 1, 1B, 1C:
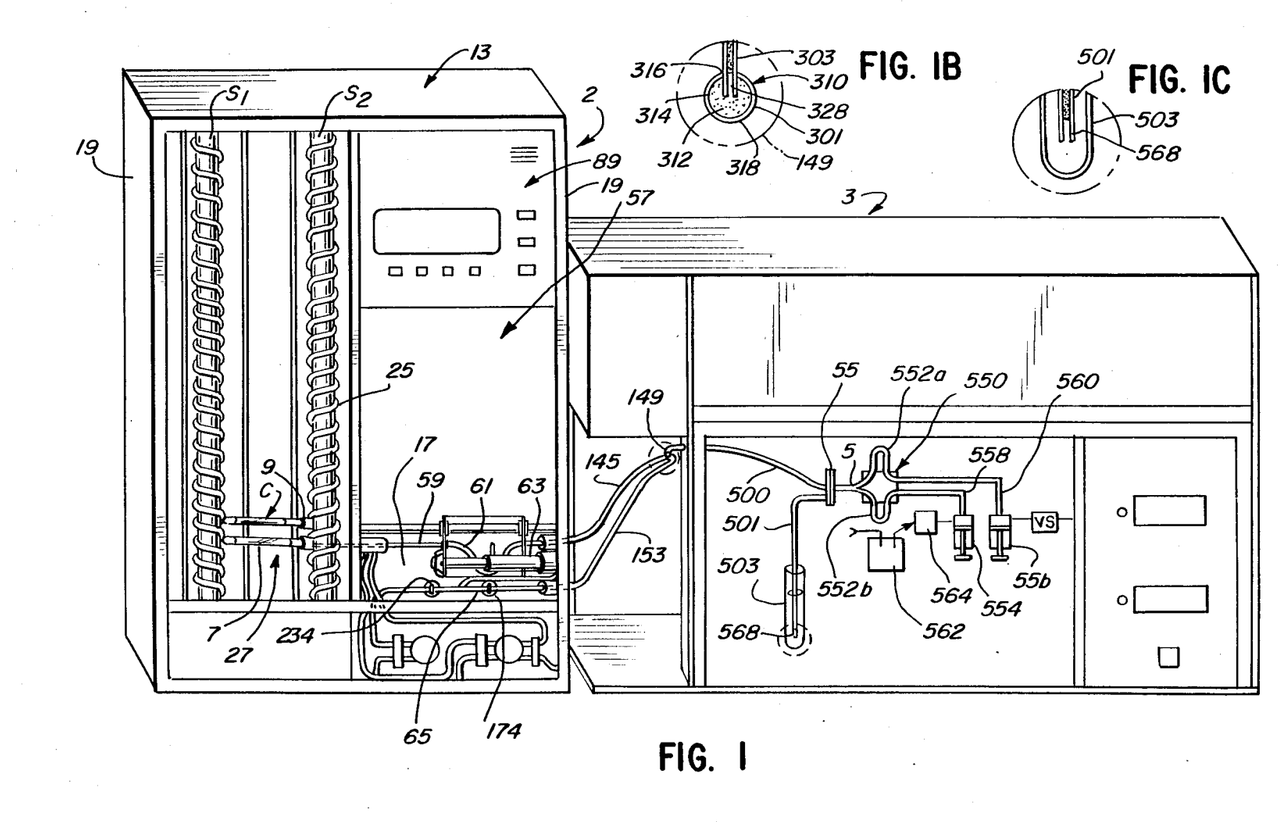
FIG. 1 is a front elevational view in which a sampler apparatus of the present invention for obtaining a sample of blood or the like from a closed container is shown on the left, and an analyzer for analyzing the sample is shown on the right.
FIG. 1B is an enlarged view of a portion of a cross section of the T-valve of the invention.
FIG. 1C is an enlarged view of a portion of a test tube and sip tube of the manual mode portion of the sampler apparatus.

Referring now to the drawings, particularly to FIG. 1, sampler 2 and analyzer 3 apparatuses of the present invention are indicated in their entirety at 1 and represent a blood sampling-analysis apparatus described in my U.S. Pat. No. 4,311,484 which is incorporated by reference as if fully rewritten herein. Where appropriate, use of the reference numerals of the '484 patent has been continued in this specification. The sampler apparatus 2 is operable to obtain a sample of blood, for example, in a closed container C at a pressure less than atmospheric pressure and to deliver it to an analyzer 3 at a pressure near to atmospheric pressure. This enables the analyzer having intake means constituted by an intake line 5 to more readily aspirate the specimen sample through intake line 5 and into the analyzer for analysis. The fact that sampler apparatus 2 is able to deliver a sample from container C to intake line 5 at a pressure at near atmospheric permits quick and easy aspiration of the sample by the analyzer into intake line 5 under conditions similar to those which apply to the manual aspiration mode.

Sample apparatus 2 is adapted for handling a series of closed containers C, each of which comprises an elongated tubular body or tube 7 enclosed at one end and having its other end stopped with a rubber plug 9 having a diameter greater than that of the tube. The sampler apparatus 2 comprises a cabinet 13 having control box 89; cabinet 13 having door 15, side wall 19 and a support wall 17. A pair of substantially parallel vertical shafts S1 and S2 are mounted for rotation within cabinet 13 behind transparent door 15. Shafts S1 and S2 are screw-threaded as at 25 and constitute means for conveying a series of closed containers C downwardly and generally in horizontal position to a sampling station 27, and for imparting a gentle rocking and rotating motion to the containers as they are being so conveyed thereby to obtain a substantially uniform mix or distribution of particles (e.g., blood cells) contained therein.

Shaft S1 and S2 are operable to rotate in one direction and then the other direction a predetermined number of times causing the stoppered right ends of the container C between screw shafts and threads 25 to rock up and down relative to the opposite end of the tube and rotate to effect mixing of the blood in the containers.

Sample apparatus 2 is equipped with an aspiration and transfer system 57 for aspirating a specimen sample from each container C when it reaches sampling station 27 and for then delivering part of the sample to the intake line 5 of analyzer 3. This system 57 comprises means 59 for penetrating the puncturable stoppered (right) end of the container C at sampling station 27, conduit 61 connecting penetrating means 59 line or auto-sip tube 500 which is a line from the sampler apparatus to the analyzer for the automated aspiration mode of the analyzer, and an aspirator or syringe 63 constituting means for reducing the pressure in conduit 61 when the penetrating means has punctured the container C to aspirate a specimen sample from the container for delivery to line 500. The aspirator communicates with conduit 61 via a second conduit 65. As will appear, the pressure in the first conduit 61 increases following aspiration of the specimen sample from container C enabling the sample readily to be drawn by the analyzer through line 500.

The sampler 2 is connected to the analyzer 3 generally through conduit 61 which includes line 145 and second conduit 65 which includes line 153; lines 145, 153 and 500 all being joined at tee 149 having T-valve 300 (FIG. 4) therein, which will be described in more detail infra.

Penetrating means 59 comprises an elongate horizontally disposed needle 67 having a passage 69 therein (FIG. 2) extending its entire length. The needle is open at its left and right ends to provide an inlet and outlet for entry of the specimen sample into passage 69 and for exit of the sample therefrom into conduit means 61 which is connected to the outlet end of needle 67. A carriage means indicated generally at 77 is provided for moving the needle from a retracted position in which the inlet of the needle is exposed to atmosphere, to an extended position in which it penetrates the stoppered end of container C at sample station 27 with the needle inlet in position for entry of specimen sample into the needle passage 69. Carriage 77 is also operable to move needle 67 back to its retracted position after termination of a predetermined aspiration period (four seconds, for example). Movement of the needle from its retracted to its extended position and then back to its retracted position after aspiration constitutes an aspiration cycle.

Figure 2:
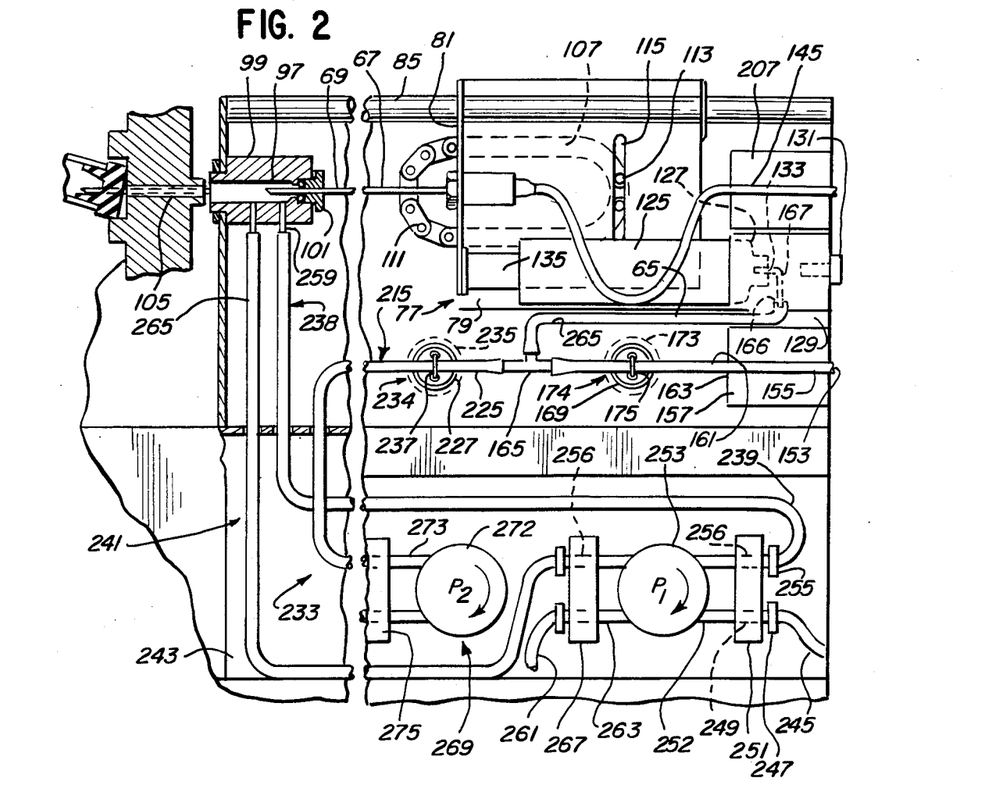
FIG. 2 is an enlarged view of a portion of FIG. 1 with the penetrating means being shown in retracted position.
Figure 3:
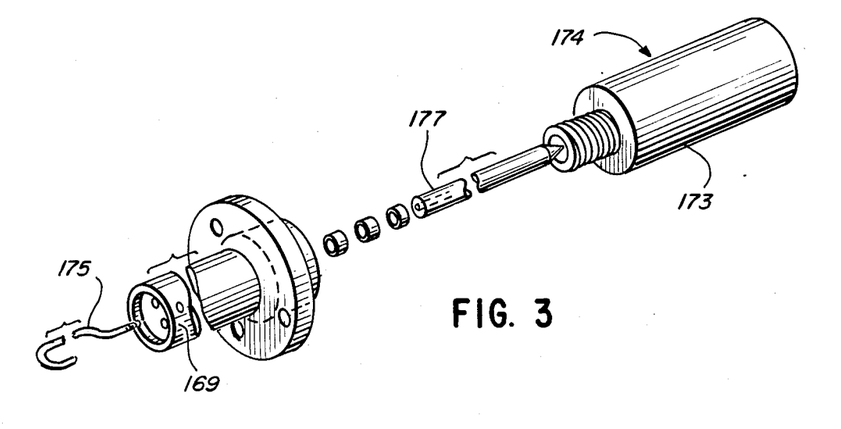
FIG. 3 is an enlarged exploded perspective view of a portion of FIG. 2.

Carriage 77 comprises a carriage in the form of a vertically disposed rectangular carriage plate 79 extending in side-by-side direction with respect to the cabinet and having a pair of forwardly extending vertical flanges 81 at its left and right sides. The carriage is slidable back and forth on a horizontal guide rod 85 extending generally parallel to the support wall of the cabinet. Suitable bearings mounted in carriage flanges 81 receive guide rod 85 therethrough for facilitating sliding of the carriage on the guide rod.

Needle 67 is suitably mounted on the left carriage flange 81 and extends horizontally and to the left therefrom through a horizontal bore 97 in a needle guide block 99. The diameter of bore 97, which is counterbored at its right end, is only slightly larger than the diamter of the needle. A nipple 101 threaded into the right end of bore 97 has a hole in it generally coaxial with bore 97 for receiving needle 67 therethrough and guiding it as it moves between its extended and retracted positions. As will more fully be explained hereinafter, bore 97 in the needle guide block constitutes a rinsing chamber in which the outer surface of the needle is washed as it moves from its extended back to its retracted position and for a brief time thereafter. When in its extended position, the needle extends through a diametrical bore 105 in the threaded screw 25 of the right shaft S1 and penetrates the puncturable end of the closed container C at the sampling station for aspirating a specimen sample therefrom. The sample is aspirated through the inlet of the needle passage 69, and the outlet, and into conduit means 61 for delivery to intake line 5 of the analyzer via line 500.

Carriage 77 further includes drive means 107 for reciprocating the carriage 77 along the guide rod 85 to move the needle between its extended and retracted positions. Drive means 107 comprises an electric motor with a chain-and-sprocket drive 111, and a pin 113 on the chain of the drive receivable in a vertical slot 115 in carriage plate 79. As this pin 113 moves along the oblong path defined by the chain-and-sprocket drive, the carriage and needle are reciprocated between retracted and extended positions. Two L-shaped brackets are mounted on the carriage adjacent to its upper horizontal edge and extend in a horizontal plane rearwardly from the carriage toward support wall of the cabinet. When the carriage is in its fully retracted position, the right bracket interrupts the light beam of a sensor mounted on the support wall of the cabinet adjacent to control post 89, and when the carriage is in its fully extended position the left bracket interrupts the light beams of a sensor mounted on the front wall of the cabinet. Brackets and are slidably adjustable in the horizontal direction with respect to the carriage.

Aspirator 63, which may be a syringe, comprises a cylindrical barrel 125 mounted in horizontal position with its right end secured in a cylindrical recess 127 in a cylindrical block 129, the latter being mounted with a screw 131 to the side wall 19 of the cabinet. The barrel 125 constitutes cylinder means and has an opening 133 at its right end in communication with conduit 65. A piston 135 is movable axially in the barrel between a retracted position in which it is relatively close to the right end of the barrel and an extended position in which it is further away from the right end of the barrel. The piston is mounted on the carriage for movement therewith. As the carriage slides to the left on guide rod 85 toward its extended position, piston 135 moves from its retracted to its extended position to produce a negative pressure in conduit means 65, and as the carriage slides to the right back toward its retracted position, the piston also moves back to its retracted position.

Conduit 61 connecting the outlet of the needle passage 69 and line 500 and via aspiration mode valve 55 to line 5 of the analyzer 3 comprises a line of flexible tubing 145 connected at one end to the right end of needle 67 and at its other (right) end to to one end of resilient tube 301 of the T-valve, 300. The line 500 is connected to one end of a rigid tube 303 of valve 300 and at its other end the aspiration mode valve 55.

Second conduit 65 extends from T-valve 300 to the opening 133 at the right end of barrel 125 of the aspirator. It comprises a line 153 of flexible tubing extending to the T-valve from the inlet 155 of a sensor 157. A line 161 of flexible tubing connects the outlet 163 of sensor 157 with a T-nipple 165 another arm of which is connected via tube 265 to nipple 166 in syringe block 129, and via passage 167 to a cylindrical recess 127 in which the right end of barrel 125 is received.

Line 161 which connects the outlet 163 of sensor 157 to T-nipple 165 is passed through holes on hub 169 of sample pinch valve 174 mounted on support wall of the cabinet. Sample valve 174 comprises a solenoid 173 having a pincher 175 attached to plunger 177, the plunger being biased toward an extended position by the resiliency of tubing 161 located between pincher 175 and hub 169. On energization of the solenoid, plunger 177 is operable to move rear-wardly pulling the pincher 175 against hub 169 and it pinches line 161 to close it. The solenoid is adapted to close line 161 as the needle 67 and piston 135 are moved by carriage 77 from their retracted to their extended positions, thereby enabling the aspirator to develop a negative pressure in passage 167 and tube 265 and in the portion of line 161 between nipple 165 and plunger 177. The sample valve 174 is deenergized to open line 161 when the needle reaches its extended position inside container C thereby reducing the pressure in needle passage 69 and conduit means 61 and 65 to permit aspiration of a specimen sample from the closed container for delivery to intake line 5 of the analyzer.

Sensor 157 is responsive to the flow of the leading end of an aspirated specimen sample therepast for generating a signal to actuate solenoid 173 of valve 174 to close line 161.

When a sample of blood or the like is aspirated from container C through sensor 157 and after a brief time delay, the sensor sends a signal to sample valve 174 to close line 161 and prevent further aspiration.

During the aspiration period, it is desirable to have means for detecting air bubbles in the specimen sample drawn into conduit means 61 so that during subsequent aspiration by analyzer 3, an uninterrupted segment of whole blood is present in the metering loops of the analyzer whole-blood metering valve. Conductivity sensor 207 represents such means. This sensor is mounted to right wall 19 and in tubing 145 above syringe block 129 is responsive during the aspiration period to the occurrence of air-bubbles in the tubing for signalling (e.g., sounding) an alarm. More particularly, sensor 207 comprises two electrodes spaced apart in tubing 145. If during aspiration of a whole-blood sample in tubing 145 no air bubble passes sensor 207 and no alarm is signalled, the sensor indicates that there is a continuous specimen sample for aspiration by analyzer 3. However, if air bubbles in tubing pass the sensor, or because the trailing end of an insufficient sample is downstream in the sensor, the sensor is adapted to signal an alarm so that the analyzer 3 may be prevented from entering its aspiration mode.

As carriage 77 moves to the right toward its retracted position following aspiration of the specimen sample from the container C at sampling station 27, piston 135 also moves to the right in barrel 125. During this latter movement of the piston, air is expelled through opening 133 in barrel 125 into passage 167 and thence to atmosphere via discharge conduit generally indicated at 215. The latter comprises a flexible discharge line 225 of tubing extending from T-nipple 165 through a hub 227 mounted on the support wall adjacent hub 169 and then downwardly to a suitable waste receptacle (not shown).

A rinse valve 234 comprising a solenoid 235 and pincher 237 identical in construction and operation to the above-described sample valve 174 for closing line 225 is mounted on the support wall adjacent solenoid valve 173. The pincher 237 of valve 234 is operable on energization of the solenoid 235 to move rearwardly to a retracted position to pinch the line 225 against the hub to close it. The solenoid is energized to close the discharge line 225 before the carriage 77 and piston 135 thereon move leftwardly from their retracted to their extended positions, thereby enabling a negative pressure to be developed as the piston moves to the left in barrel 125. Rinse valve 234 is deenergized to open line 225 after termination of an aspiration period and before the carriage and piston move back to their retracted positions, thereby enabling fluid to be expelled from the system via discharge conduit means 215 as the piston moves to the right in the barrel. The aspiration and transfer system also includes means generally indicated at 238 for cleaning the outer surface of the needle as the latter moves from its extended back to its retracted position and for a brief interval thereafter. This is necessary to remove blood or other matter from the needle so that contamination of one specimen with particles or cells from another is avoided. Cleaning means 238 comprises the rinsing chamber 97 in the needle guide block 99 described above, a line 239 for supply of a suitable cleaning fluid (such as an 0.85% NaCl) solution to the chamber, a line 241 for drainage of the chamber, and a pump $P_1$ (FIG. 2) operable to pump cleaning solution through the supply line 239 to the rinse chamber and thence through the drain line 241 to a waste receptacle (not shown). Pump $P_1$ is preferably a peristaltic pump of the type well known in the art and is secured to a mounting plate 243 fastened to the back of the cabinet below carriage 77 and the syringe block 129. Supply line 238 comprises three sections, a first section 245 connected at one end to a source (not shown) of cleaning solution and at its other end to a nipple 247 received in one end (the left end as viewed in FIG. 2) of a horizontal bore 249 (FIG. 2) through a retaining bar 251 bolted to mounting plate 243, a second section 252 of resilient material extending around the head 253 of pump $P_1$ and having one end secured to nipple 247 and its other end secured to a nipple 255 in the right end of a second horizontal bore 256 through retaining bar 251, and a third section 239 connected at one end to nipple 255 and at its other end to a metal connecting tube 259 communicating with rinse chamber 97. Similarly, drain line 241 also comprises three sections 261, 263 and 265, the middle section 263 being of resilient material and extending around pump head 253. The three sections of drain line 241 are coupled via a retaining bar 267 in the same manner described above in regard to supply line 239. On actuation of pump $P_1$, the pump head 253 rotates in an clockwise direction to sequentially compress and release sections 252 and 263 of the supply and drain lines, thereby achieving a peristaltic pumping action for circulating cleaning solution through the rinse chamber to clean the outside surface of the needle as it moves from its extending back to its retracted position. For reasons which appear below, the pump remains in operation for a brief interval of time after the needle reaches its fully retracted position in which the tip of the needle is between supply and drain lines 239 and 265.

Means generally designated 269 is operable in conjunction with cleaning means 238 for automatically flushing and cleaning needle passage 69, first and second conduits 61 and 65, and discharge conduit 215 after completion of an aspiration cycle, which, as mentioned above, comprises movement of the carriage and needle from their retracted to their extended positions, aspiration of a specimen sample from a container at sampling station 27, and movement of the carriage and needle back to their retracted positions. More specifically, means 269 comprises a second peristaltic pump $P_2$ secured to mounting plate 243. This pump comprises a pump head 272 rotatable in a clockwise direction to repetitively compress and release a resilient section 273 of line 233 extending around the pump head and having its end secured in a retaining bar 275 identical to retaining bars 251 and 267 described above. Thus the requisite peristaltic pumping action is produced to draw cleaning solution from rinse chamber 97 into needle passage 69 and thence through first and second conduit means 61, 65 and discharge conduit means 215 to a sizable waste receptacle. This flushes and cleans the entire system preparatory to the initiation of the next aspiration cycle. Additionally, as will be more fully described infra, pump $P_2$ captures the back-wash solution from the analyzer.

Figures 4, 5, 6, 7:
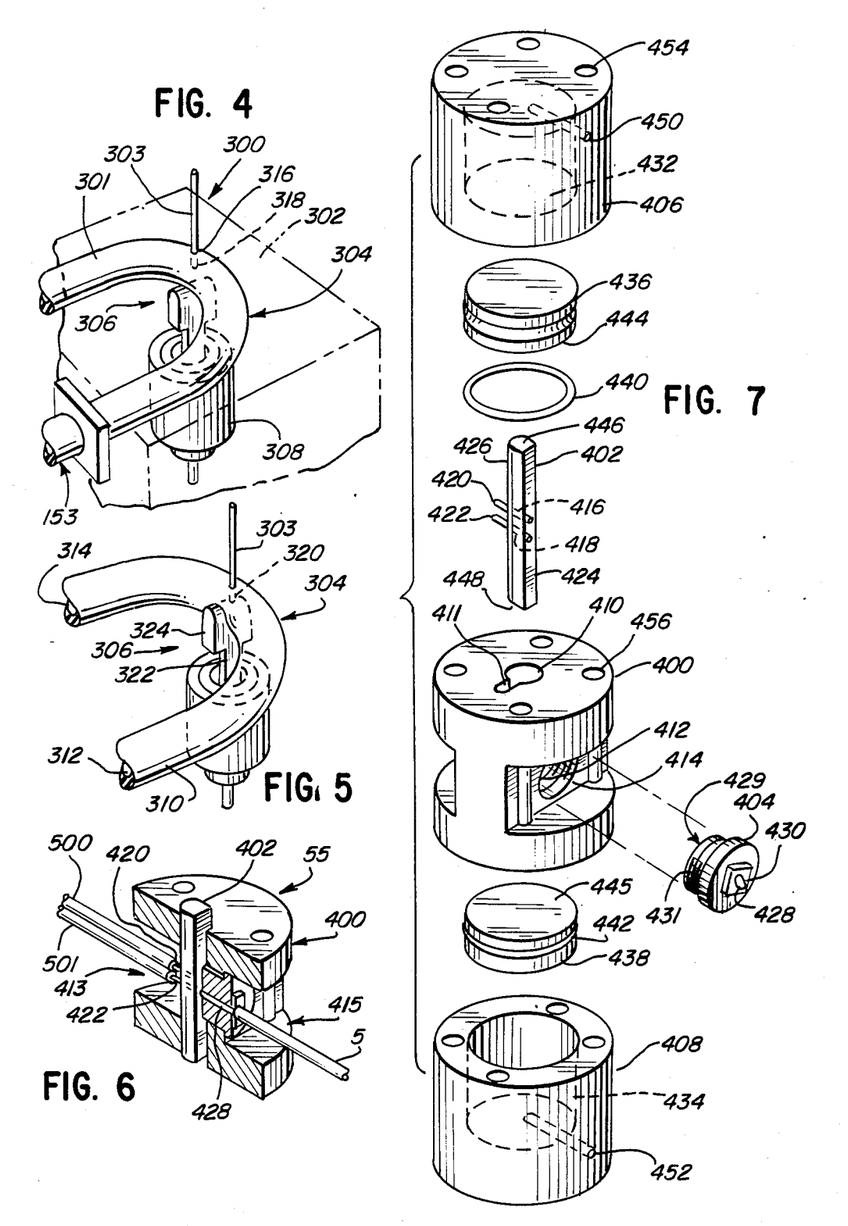
FIG. 4 is an enlarged perspective view of the T-valve of the invention in the open position.
FIG. 5 is an enlarged perspective view of the T-valve of the invention in the closed position.
FIG. 6 is an enlarged perspective cross section of the reciprocating sliding valve.
FIG. 7 is an enlarged exploded drawing of the reciprocating sliding valve.

Turning now to FIGS. 4 and 5, T-valve 300 includes line or tube 301 in housing 302 which line is a resilient tube which joins lines 145 and 153 or it may be a part of such lines in a U-shaped loop 304; rigid tube 303 which joins line 500 into the analyzer at aspiration mode valve 55; and a means for deforming the resilient tube, the deformation means including movable pinch member 306 operably connected to air cylinder 308 for reciprocal motion transverse to the longitudinal axis to the resilient tube 301. Resilient tube 301 is made from resilient tubing material of cylindrical cross section such as resilient silicone rubber tubing. The resilient tube has exterior wall 310, defines a cylindrical passage 312 with interior wall 314. A small hole 316 extends through the side wall of the resilient tube 301 opposite the solenoid and its pinch member. Rigid tube 303 has a generally cylindrical cross section, is generally normal to the plane formed by loop 304 and has orifices at each end and is made from a hard and rigid material, such as stainless steel or polyvinylchloride. It extends through the hole 316 in resilient tube 301 with an orifice 318 at the end tip 320 of tube 303 extending about half way through resilient tube 301 at the center of the cylindrical passage of the resilient tube, the longitudinal axis of rigid tube 303 being transverse to the longitudinal axis of resilient tube 301.

The air cylinder is actuated via a solenoid valve with circuitry like that used to actuate valves 174 and 234. The pinch member 306 includes a stem 322 and a blade 324, the stem being operably connected to the air cylinder 308. The blade is transverse to the longitudinal axis of resilient tube 301 and is in generally the same plane as the longitudinal axis of rigid tube 303. Preferably the width of the blade pinch member is equal to or slightly greater than the diameter of the tube.

Upon actuation of the air cylinder at the open position of the T-valve, the pinch member moves transversely to the longitudinal axis of resilient tube 301 toward the orifice of rigid tube 303, and as seen in FIG. 5, thrusting the inner wall 314 of the resilient tube 301 against the orifice of 318 of the rigid tube sealing rigid tube 303 from resilient tube 301, but permitting a flow of fluid through resilient tube 301 after such sealing. Hence after closing the T-valve liquid or blood may flow through tube 301 with a reduced cross section, but liquid is not permitted to flow from resilient tube 301 into and through rigid tube 303 to analyzer 3.

Turning now to FIGS. 6 and 7, the aspiration mode valve 55 is a reciprocating sliding valve which channels blood to line 5 and samples either from the automated sampler which sequentially withdraws blood from a plurality of samples or through line or sip tube 501 from individual container 503 in a manual aspiration mode. The reciprocating sliding valve includes a housing 400; a sliding member 402, valve seat 404 and a means for activating the sliding member which includes activating air chambers 406 and 408.

The housing 400, which may be made of polytetrafluoroethylene commercially known and available as Teflon or other durable material, includes a longitudinal channel 410 for receipt of the sliding member 4 stem clearance slot 411 adjacent to and running the length of longitudinal channel 410 and valve seat channel 412 for receipt of valve seat 404 which is generally normal to longitudinal channel 410. Threads 414 in valve seat channel 412, as will hereinafter be described, threadably engage threads on valve seat 404. As will be described more fully infra, slots 413 and 415 in the housing permit reciprocation as well as access to the sliding member, and access to the valve seat, respectively.

Sliding member 402, which is made of stainless steel or the like, is an elongated cylinder adapted to fit into longitudinal channel 410 in the housing and slidably frictionally engages the internal walls of that channel. The sliding member has two parallel longitudinal channels 416 and 418 which generally are normal to the longitudinal axis of the sliding member and longitudinal channel 410 in the housing and are adapted to have blood, air or saline flow therethrough. Stems 420 and 422 are generally normal to the longitudinal axis of the sliding member and the longitudinal channel 410 and extend from channels 416 and 418 respectively. Stem 420 interconnects channel 416 with line 500 and the sampler 2; stem 422 interconnects channel 418 with line 501 and container 503 in manual aspiration mode. The side of the sliding member opposite the stems has a flat planar face 424 extending the length of the sliding member for abutting engagement with valve seat 404. The stems extend from the rounded area 426 of the body of the cylindrically shaped sliding member.

Valve seat 404, which may be made of polytetrafluoroethylene or any other durable material, is a cylindrically shaped plug which fits into valve seat channel 412. A longitudinal channel 428 extends longitudinally through the center of the plug from planar face 429 to the opposite face, the channel 428 terminating in nozzle 430. The seat has threads 431 for interengagement with threads 414 in valve seat channel 412. With insertion of the valve seat into the valve seat channel and threads 431 and 414 interengaged, planar face 429 of the seat abuttingly engages the planar face 424 of sliding member 402 which not only aligns the sliding member with the seat, but aligns the sliding member in longitudinal channel 410 in the housing. Longitudinal channel 428 in the seat terminates in nozzle 430 which interconnects the channel in the valve seat with line 5 into the analyzer. The seat and channel 428 interconnects line 5 into the analyzer with line 500 into the sampler 2 through channel 416 and stem 420 in the sliding member, or it interconnects line 5 into the analyzer with sip tube 501 and tube or container 503 through channel 418 and stem 422 on the sliding member. Line 5 interconnects the aspiration mode valve 55 with metering valve 550 and metering loops 552a and 552b of that valve which separates and meters the amount of blood samples for various blood dilutions and analyses as is known.

The air activating chambers of the actuating means include piston cylinders 432 and 434 fitted with pistons 436 and 438 which have side walls with sealing rings 440 and 442. The faces 444 and 445 of the pistons abuttingly engage the ends 446 and 448 of the sliding member upon actuation of the actuating means. The piston cylinders 432 and 434 have air ports 450 and 452, respectively, for the transportation of air into and out of piston cylinders 432 and 434. These ports are connected to an air source and vent (not shown). When air is transported into the piston cylinder, the piston will be driven into an end of the sliding member pushing it into a position wherein channel 428 in the seat is aligned with channel 416 or channel 418 in the sliding member. Slot 413 in the housing permits the sliding reciprocation of the sliding member in the housing with stems 420 and 422 extending into the slot. Slot 415 in the housing permits access to nozzle 430 on seat 404. Holes 454 permit a fastener to extend through the air chambers to affix the chambers to the housing via housing holes 456.

In standby status the aspiration mode valve interconnects the analyzer with container or tube 503 through manual-sip tube 501. A controller in the sampler (not shown), generates a signal to the actuating means to push the sliding member upwardly with piston 445 such that the analyzer valve provides a direct and straight fluid flow by connecting line 5 with line 501 through channels 418 and 428 in the sliding member and valve seat respectively.

Figures 8, 8A:
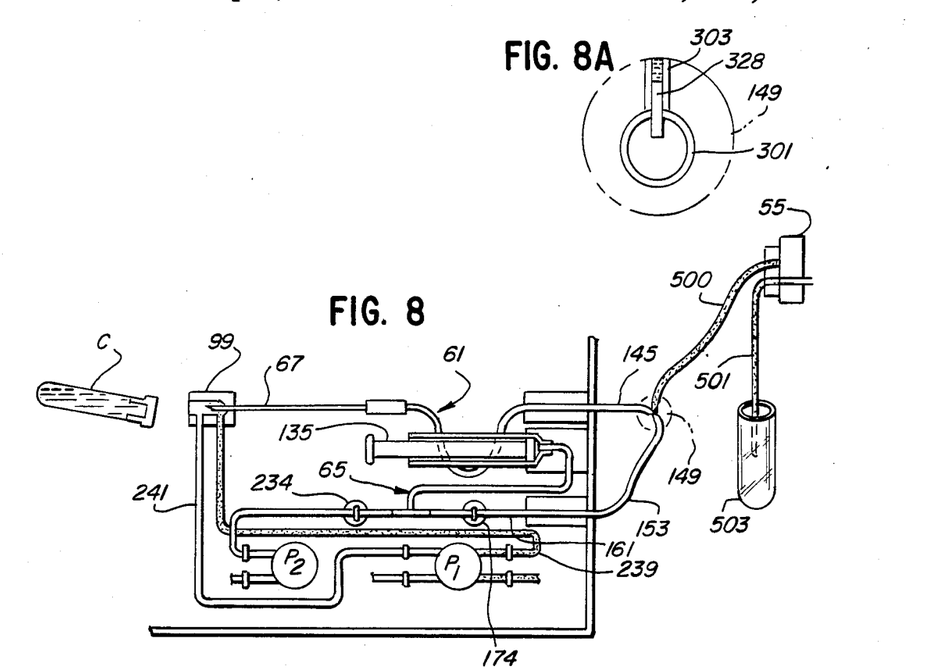

Turning to FIGS. 8 through 12 the cycle of the sampler in conjuction with the analyzer will be discussed. FIG. 8 illustrates the standby status with air in needle 67, and lines 145 and 153; line 500 being almost filled with saline backwash liquid shown in broken line. As seen in FIG. 8A, there is a small air bubble 328 in tube 303 and part of tube 500 the formation of which is explained infra.

At rest, as seen in FIGS. 1 and 8 line 5 is connected through aspirator mode valve 55 to manual-sip tube 501 for drawing liquid samples from tube 503 into metering loop valve 550 which splits the blood sample into two parts in lines 552a and 552b for dilution and analysis. Loop valve 550 is connected to pumps 554 and 556 through lines 558 and 560 (FIG. 1). A saline wash source 562 is connected to lines 558 and 560 under pressure, the access of the saline wash to the lines being controlled by valve 564. Pumps 554 and 556 draw blood into the analyzer, as will be described infra. After analyzer aspiration cycle saline wash source 562 supplies a saline back wash through loops 552a and 552b, line 5 and line 500 or 501 for automated or manual aspiration mode respectively with the opening of valve 564. At rest air is in lines 67, 61, 65 and 215.

Figures 9, 9A:
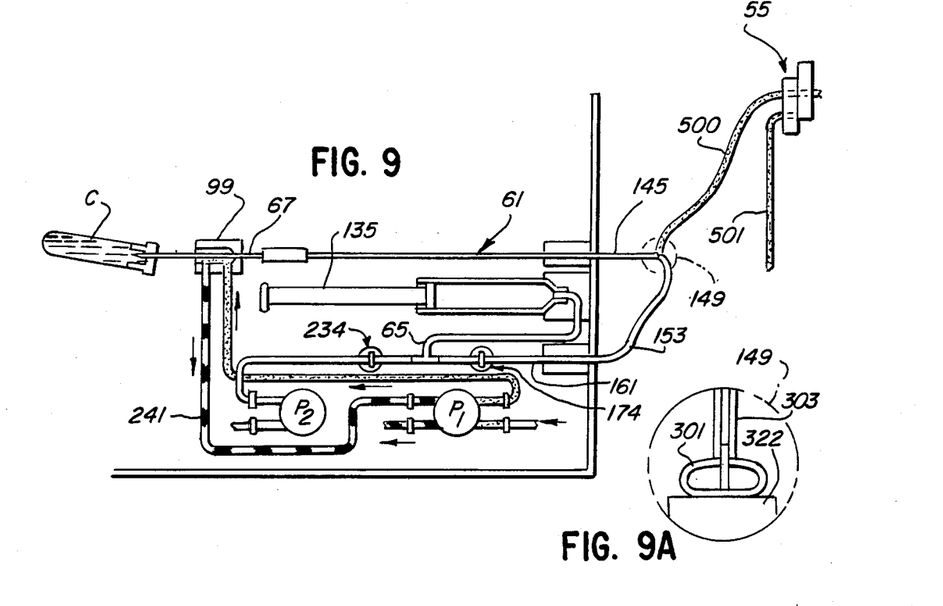

As shown in FIGS. 9 and 9B at the beginning of the automated aspiration cycle, aspiration mode valve 55 is extended to the auto-sip position to connect line 5 with line 500 through valve 55, valves 174 and 234 are closed with pinchers 175 and 237 respectively and the T-valve 300 being closed by blade 324 of plunger 306 (FIG. 9A). FIG. 9 illustrates the needle 67 being thrust into container C with piston 135 being withdrawn. This creates a vacuum in the system through lines 65. With the vacuum, sample valve 174 is opened with the needle in the container, see FIG. 10.

Figures 10, 10A:
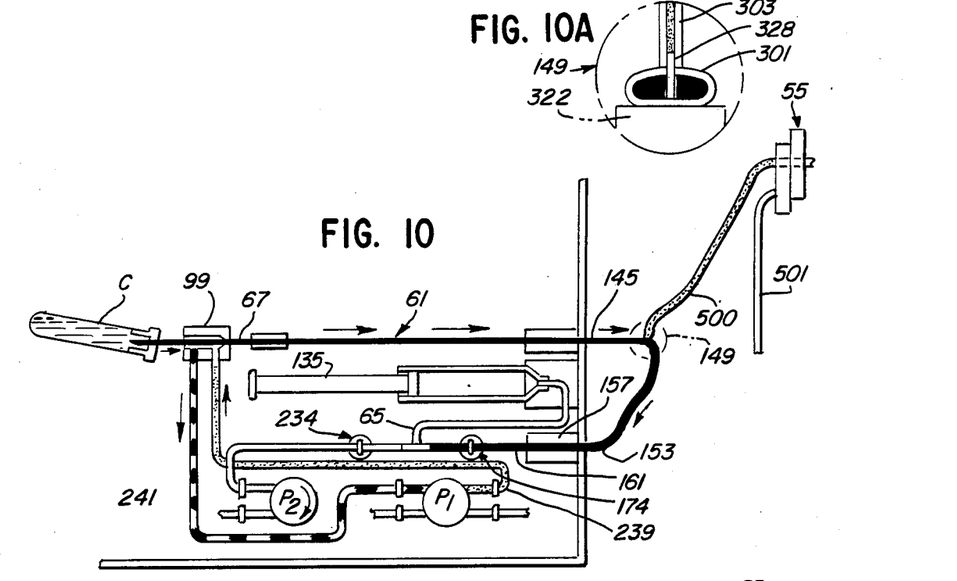

As seen in FIGS. 10 and 10A, with the opening of 174 the vacuum pulls blood (shown in solid) from the container through needle 67, then through line 61 through the T-valve (the valve being closed (FIG. 10A) thus maintaining the integrity of the air-bubble 328 in spite of the vacuum and the blood flow in tube 301 of the T-valve) into line 65 and slightly past pincher 175. Sensor 157 permits the blood to flow slightly past plunger 175 (which is extended rendering valve 174 open) at which point sensor 157 closes sample valve 174 with pincher 175 pinching 65 closed. During this operation pump $P_1$ pumps saline through line 239 to needle rinse chamber 99 through drain line 241.

Figures 11, 11A:
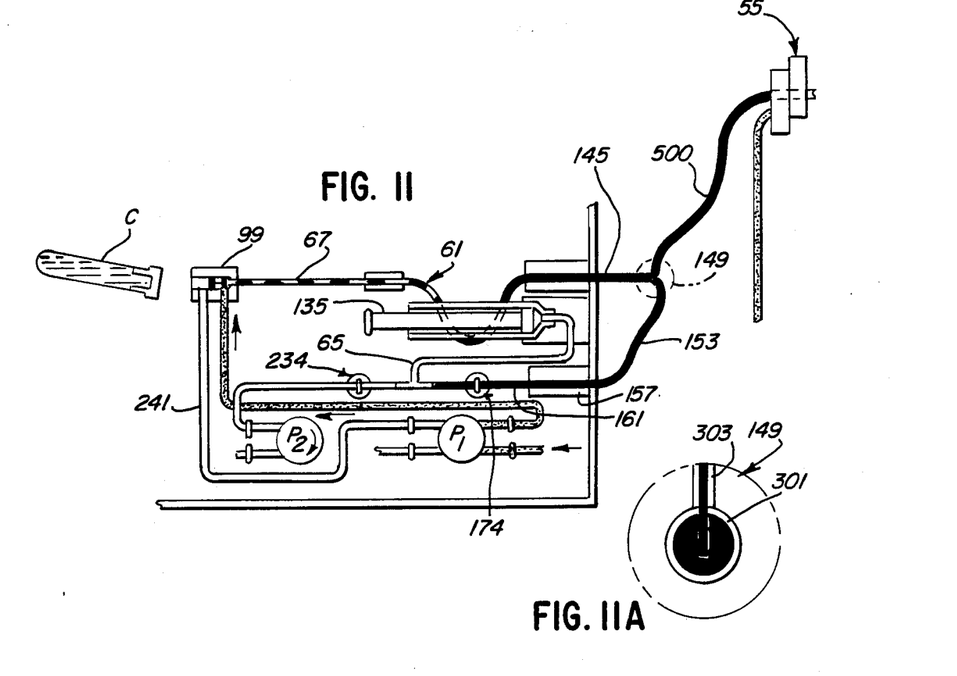
Figure 12:
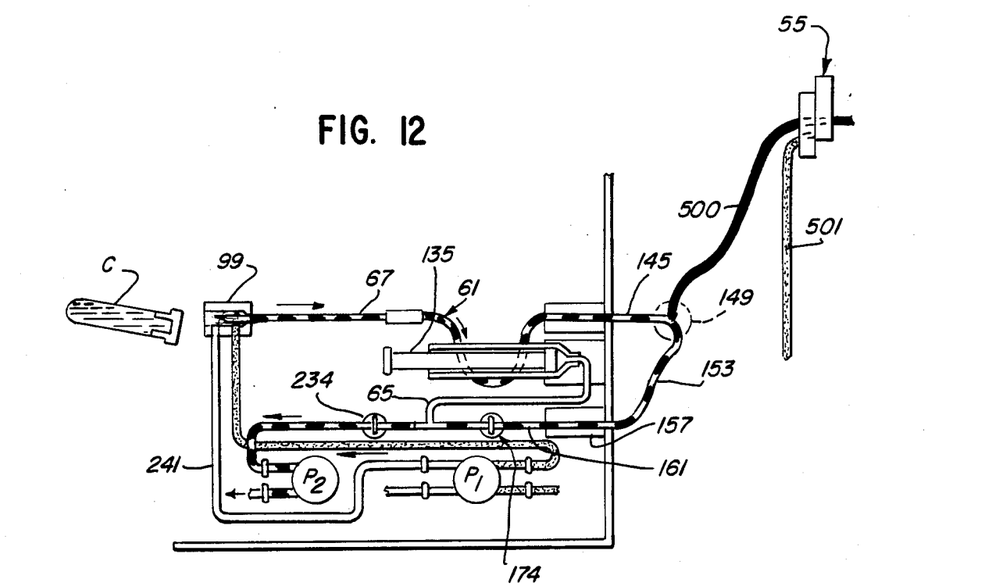
Figure 12A:
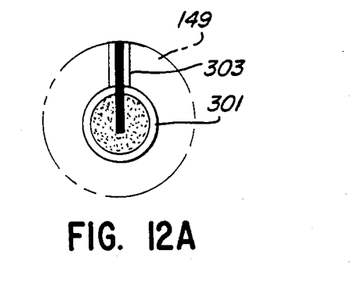

As seen in FIGS. 11 and 11A after the blood is drawn slightly past sample valve 174 and pincher 175 pinches line 161 closed, rinse valve 234 opens and pincher 237 unpinches line 215, the needle retracts and plunger 135 returns to its retracted position; valve 234 is open; sample valve 174 is closed; and piston 135 is pushed into the barrel 125 of the syringe which has pushed air out past valve 234 which air is pumped out of the system through $P_2$. At this time T-valve 300 opens (FIG. 11A), and analyzer pumps 554 and 556 draw saline and then blood (the blood being separated as it flows from the saline by air-bubble 328) from lines 61, 145, via line 500, aspiration mode valve 55 and 5 into the analyzer metering loop valve 550. Because sample valve 174 is closed little or no blood is drawn from line 153 through T-valve 300 into line 5. After about 100 microliters of blood is drawn into the analyzer 3, the pumps stop, and the analyzer metering valve 550 having blood in metering loops 552a and b to direct the blood for various blood dilutions used for blood analyses. The air bubble aids in drawing the same amount of blood through metering valve 550 because the bubble is consistently made the same size which permits the system to draw the same amount of blood through 550 and control PLD in either automatic or manual mode. After about 25 seconds the metering valve is switched to its first position, a back flush cycle starts with valve 564 opening and saline being directed through the metering loops of valve 550 through line 5, through valve 55, line 500, tube 303 of the now open T-valve and lines 153 and 215 to waste. See FIGS. 12 and 12A. During this cycle $P_2$ is drawing on the system to pull saline out to waste. After the back flush, valve 564 closes and pumps 554 and 556 start to pull saline back through lines 5 and 500 and create air bubble 328 in tube 303. After completion of the cycle, aspiration mode valve 55 returns back to the manual aspiration position connecting line 500 and metering valve 550 with manual-sip tube 501.

In the manual aspiration mode pumps 554 and 556 operate in a manner similar to that in automatic aspiration mode. Blood is pulled through sip tube 501 by the pumps into metering valve 550. The air bubble 568 in sip tube 501 being consistently made the same size as the air bubble in automatic mode which aids in PLD control.

After about 25 seconds, the metering valve is switched to its first position, a back flush cycle starts with valve 564 opening and saline being directed through metering loops of valve 550 through line 5, through valve 55 and line 501, the saline being directed out the tip of 501 to waste (not shown). After the back flush, valve 564 closes and pumps 554 and 556 start to pull saline back through line 501 and 5 to create an air bubble 568 at the end of line 501.

While the present invention has been shown and described with respect to a preferred embodiment thereof, it should be apparent that various modifications, adaptations and variations may be made utilizing the teachings of the present disclosure without departing from the scope of the invention, and are intended to be within the scope of the following claims.

Various of the features of the invention are set forth in the following claims.

What is claimed is:

1. In an apparatus for sequentially withdrawing liquid samples from a plurality of containers, transporting the samples to an analyzer and then analyzing the samples in the analyzer:

a resilient conduit having an exterior wall, a longitudinal axis and an interior passage, the interior passage adapted to have fluid flowing therethrough and being defined by an interior wall of the resilient conduit;

a second conduit from the resilient conduit to the analyzer to transport samples from the resilient conduit to the analyzer, the second conduit having at least two orifices, a longitudinal axis and an interior passage adapted to have fluid flow therethrough, the second conduit extending through the exterior wall of the resilient conduit and having at least one orifice in the interior passage of the resilient conduit;

means for periodically deforming the interior wall of the resilient conduit into sealing engagement with the orifice of the second conduit in the interior passage of the resilient conduit to sequentially separate and transport samples from the resilient conduit to the analyzer, the deforming means being exterior to the resilient conduit and including a pinch member opposite the orifice in the interior passage of the resilient conduit and means for actuating the pinch member to abuttingly engage and deform said exterior wall to sealingly engage the interior wall against the orifice in the interior passage with the resilient tube retaining an interior passage of reduced cross section for liquid flow therein.

2. An apparatus as recited in claim 1 wherein the second conduit is rigid.

3. An apparatus as recited in claim 2 wherein the longitudinal axis of the resilient conduit is substantially transverse to the longitudinal axis of the second conduit.

4. An apparatus as recited in claim 3 wherein the resilient conduit is a tube having a cylindrical cross section; the second conduit is a tube having a cylindrical cross section and the means for actuating the pinch member reciprocates the pinch member to abuttingly engage and deform the exterior wall of the resilient conduit.

5. An apparatus as recited in claim 2 wherein the resilient conduit is a tube having a cylindrical cross section; the second conduit is a tube having a cylindrical cross section and the means for actuating the pinch member reciprocates the pinch member to abuttingly engage and deform the exterior wall of the resilient conduit.

6. An apparatus as recited in claim 1 wherein the longitudinal axis of the resilient conduit is substantially transverse to the longitudinal axis of the second conduit.

7. A valve having at least two conduits for fluid flow therethrough which valve when closed permits flow of fluid through at least one conduit with reduced cross section, the valve comprising:
a resilient conduit having an exterior wall, a longitudinal axis and an interior passage, the interior passage adapted to have the fluid flow therethrough and being defined by an interior wall of the resilient conduit;
a second conduit having at least two orifices, a longitudinal axis and an interior passage adapted to have fluid flow therethrough, the second conduit extending through the exterior wall of the resilient conduit and having at least one orifice in the interior passage of the resilient conduit;
means for deforming the interior wall of the resilient conduit into sealing engagement with the orifice of the second conduit in the interior passage of the resilient conduit, the deforming means being exterior to the resilient conduit and including a pinch member opposite the orifice in the interior passage and of the resilient conduit means for actuating the pinch member to abuttingly engage and deform said exterior wall to sealingly engage the interior wall against the orifice in the interior passage with the resilient tube retaining an interior passage of reduced cross-section for liquid flow therein.

8. A valve as recited in claim 7 wherein the second conduit is rigid.

9. A valve as recited in claim 8 wherein the longitudinal axis of the resilient conduit is substantially transverse to the longitudinal axis of the second conduit.

10. A valve as recited in claim 9 where the resilient conduit is a tube having a cylindrical cross-section; the second conduit is a tube having a cylindrical cross-section and the means for actuating the pinch member reciprocates the pinch member to abuttingly engage and deform the exterior wall of the resilient conduit.

11. A valve as recited in claim 8 wherein the resilient conduit is a tube having a cylindrical cross-section; the second conduit is a tube having a cylindrical cross-section and the means for actuating the pinch member reciprocates the pinch member to abuttingly engage and deform the exterior wall of the resilient conduit.

12. A valve as recited in claim 7 wherein the longitudinal axis of the resilient conduit is substantially transverse to the longitudinal axis of the second conduit.

13. A sliding valve comprising:
a housing;
a longitudinal channel through the housing;
a cylindrical sliding member having a planar face, the sliding member extending through the channel in the housing for reciprocating movement therein, the sliding member having at least two channels which are generally normal to the longitudinal channel and which extend through the sliding member;
a valve seat which abuttingly engages the sliding member generally normal to the sliding member, the valve seat including at least one longitudinal valve seat channel which provides a generally straight fluid flow through the valve when it is aligned with one of the channels in the sliding member upon reciprocation of the sliding member in the longitudinal channel along the longitudinal axis of the channel; and
a means for actuating the sliding member for reciprocating movement of the cylindrical sliding member,
the planar face of the cylindrical sliding member being generally normal to the longitudinal valve seat channel and to the channels in the sliding member for abuting engagement of the face with the valve seat, the planar face and valve seat coacting to align the sliding member in the longitudinal channel through the housing and to align the channels in the sliding member and valve seat.

14. A sliding valve as recited in claim 13 wherein the sliding member has the valve seat abutting it on one side and stems extending from the opposite side of the sliding member from the longitudinal channels for fluid communication through the valve.

15. A sliding valve as recited in claim 14 wherein the means for actuating the sliding member includes two activating chambers at each end of the sliding member, a piston disposed in each of the chambers for an abutting relation with the end of the sliding member and a port in each of the activating chambers for the transmission of fluid in and out of the chambers for reciprocation of the sliding member.

16. A sliding valve as recited in claim 13 wherein the means for actuating the sliding member includes two activating chambers at each end of the sliding member, a piston disposed in each of the chambers for an abutting relation with the end of the sliding member and a port in each of the activating chambers for the transmission of fluid in and out of the chambers for reciprocation of the sliding member.

17. In combination in an apparatus for sequentially withdrawing a blood sample from a sample container which is part of a plurality of sample containers or withdrawing blood from individual containers in a manual mode, transporting the sample to an analyzer and then analyzing the sample in the analyzer:

a T-valve between the sample container and the analyzer, the T-valve comprising a resilient conduit having an exterior wall, a longitudinal axis and an interior passage, the interior passage adapted to have blood flowing therethrough and being defined by an interior wall of the resilient conduit;

a rigid second conduit from the resilient conduit to the analyzer to transport blood samples from the resilient conduit to the analyzer, the second conduit having at least two orifices, a longitudinal axis substantially transverse to the longitudinal axis of the resilient conduit and an interior passage adapted to have blood flow therethrough, the second conduit extending through the exterior wall of the resilient conduit and having at least one orifice in the interior passage of the resilient conduit;

means for periodically deforming the interior wall of the resilient conduit into sealing engagement with the orifice of the second conduit in the interior passage of the resilient conduit to sequentially separate and transport blood samples from the resilient conduit to the analyzer, the deforming means being exterior to the resilient conduit and including a pinch member opposite the orifice in the interior passage of the resilient conduit and means for actuating the pinch member to abuttingly engage and deform said exterior wall to sealingly engage the interior wall against the resilient tube retaining an interior passage of reduced cross-section for blood flow therein; and a sliding analyzer valve between the T-valve and the analyzer, the analyzer valve comprising a housing;

a longitudinal channel through the housing;

a sliding member extending through the channel in the housing for reciprocating movement therein, the sliding member having at least two channels which are generally normal to the longitudinal channel and which extend through the sliding member;

a valve seat which abuttingly engages the sliding member generally normal to the sliding member, the seat including at least one longitudinal channel which provides a generally straight fluid flow through the valve when it is aligned with one of the channels in the sliding member upon reciprocating movement thereof; and a means for actuating the sliding member for reciprocating movement so as to put the analyzer in fluid communication with the T-valve or a sample container in the manual mode.

18. A combination as recited in claim 17 wherein the sliding member of the sliding analyzer valve has the valve seat abutting it on one side and stems extending from the opposite side of the sliding member from the longitudinal channels for fluid communication through the valve.

19. A combination as recited in claim 18 wherein the sliding member is a cylinder with a planar face for abutting engagement with the valve seat, which face and seat coact to align the channels in the sliding member and valve seat.

20. A combination as recited in claim 19 wherein the means for actuating the sliding member includes two activating chambers at each end of the sliding member, a piston disposed in each of the chambers for an abutting relation with the end of the sliding member and a port in each of the activating chambers for the transmission of fluid in and out of the chambers for reciprocation of the sliding member.

* * * * *